(12) United States Patent
Eggink et al.

(10) Patent No.: US 10,201,148 B2
(45) Date of Patent: Feb. 12, 2019

(54) PEPPER WITH INCREASED BRIX LEVEL

(71) Applicant: RIJK ZWAAN ZAADTEELT EN ZAADHANDEL B.V., De Lier (NL)

(72) Inventors: Pieter Martijn Eggink, De Lier (NL); Jacob Pieter Willem Haanstra, De Lier (NL); Evert Willem Gutteling, De Lier (NL)

(73) Assignee: RIJK ZWAAN ZAADTEELT EN ZAADHANDEL B.V., De Lier (NL)

(*) Notice: Subject to any disclaimer, the term of this patent is extended or adjusted under 35 U.S.C. 154(b) by 32 days.

(21) Appl. No.: 14/979,884

(22) Filed: Dec. 28, 2015

(65) Prior Publication Data

US 2016/0115496 A1 Apr. 28, 2016

Related U.S. Application Data

(63) Continuation-in-part of application No. PCT/EP2014/064117, filed on Jul. 2, 2014.

(30) Foreign Application Priority Data

Jul. 2, 2013 (EP) .................................... 13174797

(51) Int. Cl.
*A01H 5/08* (2018.01)
*C12Q 1/68* (2018.01)
*A01H 6/82* (2018.01)
*A01H 1/04* (2006.01)
*C12Q 1/6895* (2018.01)
*A01H 5/00* (2018.01)
*C07K 14/415* (2006.01)
*A23L 19/00* (2016.01)

(52) U.S. Cl.
CPC .............. *A01H 6/822* (2018.05); *A01H 1/04* (2013.01); *A01H 5/08* (2013.01); *C12Q 1/6895* (2013.01); *A01H 5/00* (2013.01); *A23L 19/00* (2016.08); *C07K 14/415* (2013.01); *C12Q 2600/13* (2013.01)

(58) Field of Classification Search
None
See application file for complete search history.

(56) References Cited

U.S. PATENT DOCUMENTS

2006/0195921 A1 8/2006 Van Der Heiden
2014/0289885 A1 9/2014 Van Der Heiden

FOREIGN PATENT DOCUMENTS

WO 2004/089067 10/2004

OTHER PUBLICATIONS

Lefebvre et al. Genome 38: 112-121 (1995).*
Ben Chaim et al. Theoretical and Applied Genetics 102: 1016-1028 (2001).*
Paran et al. Molecular Biology 13: 251-261 (2004).*
Wu et al. Theoretical and Applied Genetics 118: 1279-1293 (2009).*
Eggink et al. Theoretical and Applied Genetics 127(2): 373-390 (2014).*
Chae et al. Capsicum and Eggplant Newsletter 22: 121-124 (2003).*
Albrecht et al. HortScience 45(8): S289-S290 (Aug. 2010).*
Kim et al. Weon'ye Gwahag Gi'sulji 28(6): 1014-1024 (2010) Abstract Only.*
Chinese First Office Action dated Feb. 14, 2017, which issued during prosecution of Chinese Application No. 201480037542.4.
Jiang, et al. "Study on the antioxidant activities of water-soluble polysaccharides from chilli and chilli food" Science and Food Technology, 2012, 33(11):127-129.
International Search Report and Written Opinion of the International Searching Authority dated Oct. 13, 2014, which issued during prosecution of International Application No. PCT/EP2014/064117.
Database EMBL "KS23005A03 KS23 Capsicum annuum cDNA, mRNA sequence", retrieved from EBI Accession No. EM_EST:GD111402, Mar. 2009.
Database EMBL "TSA: Capsicum annuum EJ_MegaContig_17153, mRNA sequence" retrieved from EBI Accession No. EM_TSA:JW131691, Sep. 2012.
Geleta, et al. "Combining ability and heritability for vitamin C and total soluble solids in pepper (*Capsicum annuum* L.)" Journal of the Science of Food and Agriculture 86(9):1317-1320, Jul. 2006.
Matsufuji, et al. "Anti-oxidant content of different coloured sweet peppers, white, green, yellow, orange and red (*Capsicum annuum* L.)" International Journal of Food Science and Technology 42(12):1482-1488, Dec. 2007.
Taller, et al. "Graft-induced variants as a source of novel characteristics in the breeding of pepper" Euphytica 108:73-78, Jan. 1999.
Zygier, et al. "QTLs mapping for fruit size and shape in chromosomes 2 and 4 in pepper and a comparison of the pepper QTL map with that of tomato" Theoretical and Applied Genetics 111(3):437-445, Aug. 2005.

* cited by examiner

*Primary Examiner* — David T Fox
(74) *Attorney, Agent, or Firm* — Duane Morris LLP; Thomas J. Kowalski; Deborah L. Lu

(57) ABSTRACT

The present invention relates to a pepper plant (*Capsicum annuum*) that produces fruits with an increased Brix level, wherein the pepper plant may comprise a QTL, which when present leads to pepper fruits with increased Brix level, and wherein said QTL is similar to, or in particular the same as the QTL present in the genome of plants grown from seed which was deposited at the NCIMB under NCIMB number 42139, and wherein said QTL is linked to at least one marker selected from the group of SEQ ID NO:1, SEQ ID NO:3, SEQ ID NO:5, and SEQ ID NO:7 and wherein the QTL is preferably homozygously present.

29 Claims, 1 Drawing Sheet
Specification includes a Sequence Listing.

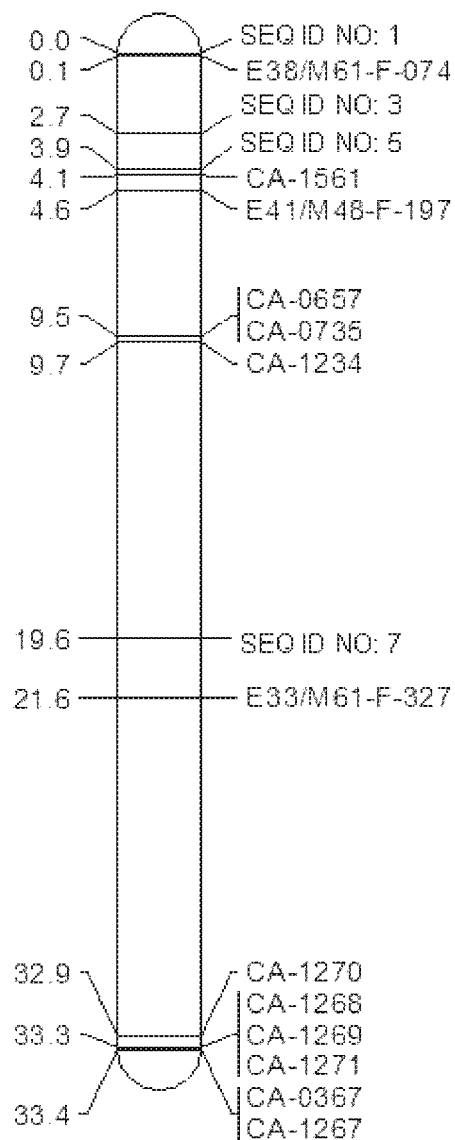

US 10,201,148 B2

PEPPER WITH INCREASED BRIX LEVEL

RELATED APPLICATIONS AND INCORPORATION BY REFERENCE

This application is a continuation-in-part application of international patent application Serial No. PCT/EP2014/064117 filed 2 Jul. 2014, which published as PCT Publication No. WO 2015/000991 on 8 Jan. 2015, which claims benefit of European patent application Serial No. 13174797.4 filed 2 Jul. 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Nov. 23, 2015, is named 43104002229_SL.txt and is 2,997 bytes in size.

FIELD OF THE INVENTION

The invention relates to pepper plants with a sweeter taste. Furthermore the invention relates to the use of plants, seeds and propagation material from the pepper plant as germplasm in a breeding program aimed at acquiring pepper plants producing fruits with a sweeter taste.

BACKGROUND OF THE INVENTION

Sweet and hot pepper plants belong to the genus *Capsicum* which is part of the Nightshade family (Solanaceae). *Capsicum* species are native to South America, Middle America and a part of North America, where they have been cultivated for thousands of years, and are now cultivated worldwide.

Some of the members of *Capsicum* are used as spices, vegetables, and medicines. The species *Capsicum annuum* is the most common and extensively cultivated of the four domesticated *Capsicum* species (*Capsicum annuum*, *Capsicum baccatum*, *Capsicum chinense*, *Capsicum frutescens*). It comprises several cultivar groups among which bell pepper (also named paprika) is the most commonly grown in northern Europe and the USA. Bell peppers or pepper fruits are eaten raw, cooked, immature and mature and may be processed into powders, sauces, and salsas. The fruits are mostly green in the immature stage, but during ripening they become red, yellow, orange, purple, or brown. Sweet pepper may comprise any pepper plants, such as bell pepper plants, having mild non-pungent fruits. Pepper plants can be cultivated in the open field, greenhouses, tunnels or shade houses under a wide range of various climatic conditions, but they will be most successful in warm and dry conditions.

Although the domesticated pepper species are of tropical origin, most *Capsicum* breeding has been carried out in temperate countries, and most have concerned *C. annuum*. Some wild species have however, been used in *C. annuum* breeding programs focusing on (mainly) disease resistance. The use of the species *C. baccatum* in *C. annuum* breeding programs has been very limited so far, since interspecific hybridization between both species is greatly hampered by post-fertilization genetic barriers. Studies with *C. baccatum* focused, therefore mainly on variation of accessions within the species, showing great variability for fruit quality characteristics, yield, resistances and bioactive compounds.

Flavor is an important quality parameter for fruits and vegetables. External qualities such as color, texture and shape are relatively easy to evaluate by both producers and consumers. However, evaluation of flavor attributes is more complex. In tomato flavor research measuring physical, biochemical and sensory properties, the latter were considered the most difficult to quantify. Flavor of fruits and vegetables, as perceived during consumption has been defined as the overall sensation provided by the interaction of taste, odor, mouth feel, sight and sound. The composition of non-volatile compounds like sugars influences mainly the sensory perceived taste, while the aroma is affected by volatile compounds.

Pepper fruits with a sweet taste are usually appreciated more by taste panel members and consumers than pepper fruits with a less sweet taste.

Citation or identification of any document in this application is not an admission that such document is available as prior art to the present invention.

SUMMARY OF THE INVENTION

It is the object of the present invention to provide novel pepper plants which produce fruits with a sweeter taste.

In the research leading to the invention, a new pepper plant of the species *Capsicum annuum* was developed that was found to comprise an introgression that leads to the production of fruits with an increased Brix level compared to fruits of isogenic pepper plants that lack the introgression. These pepper fruits were found to have a sweeter taste than the control fruits.

It is to be understood that a *Capsicum annuum* plant is phenotypically identifiable as such, though said plant may contain introgressions from other *Capsicum* species in its genome. The skilled breeder or grower knows how to distinguish *Capsicum annuum* plants and fruits from plants and fruits belonging to other *Capsicum* species.

Research that led to the present invention thus showed that the trait of producing pepper fruits with increased Brix level and a sweeter taste is caused by the presence of an introgression from *Capsicum baccatum*, identified herein as a Quantitative Trait Locus (QTL), in the *Capsicum annuum* genome. The causal QTL is as present in the genome of plants grown from seeds of which a representative sample was deposited at the NCIMB under accession number NCIMB 42139.

The present invention thus provides a pepper plant that produces fruits with increased Brix level, wherein the pepper plant may comprise a QTL, which when present leads to fruits with increased Brix level resulting in a sweeter taste, and wherein said QTL is similar to, in particular the same as the QTL present in the genome of plants grown from seed of deposit NCIMB 42139, and wherein said QTL in the genome of the deposited seeds is linked to at least one marker selected from the group of SEQ ID NO:1, SEQ ID NO:3, SEQ ID NO:5, and SEQ ID NO:7 and wherein the QTL is preferably homozygously present. Preferably, the pepper plant of the invention is a sweet pepper.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seeds of *Capsicum annuum* 11R.6956-00 that may comprise the QTL of the invention which leads to the pepper plant producing fruits that have an increased Brix level, were deposited with NCIMB Ltd, Ferguson Building, Craibstone Estate, Bucksburn, Aberdeen AB21 9YA, UK, on Apr. 12, 2013 under deposit accession number NCIMB 42139. Seeds of this deposit may comprise the QTL in a homozygous state.

The deposited seeds do not meet the DUS criteria which are required for obtaining plant variety protection, and can therefore not be considered to be plant varieties.

The Deposits with NCIMB Ltd, under deposit accession number NCIMB 42139 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 1: Genetic map of chromosome 3/linkage group 3 of the *C. annuum×C. baccatum* BC2 population.

DETAILED DESCRIPTION OF THE INVENTION

A plant of the invention thus may comprise a QTL that is similar to or the same as the QTL found in deposit NCIMB 42139. Similar in this context means that although the nucleotide sequence of the QTL in the genome of plants of the invention may not be completely identical to the corresponding nucleotide sequence in the genome of plants grown from seeds of deposit NCIMB 42139, the locus of the QTL and the phenotype of increased brix caused by it is in any case the same. Whether or not the QTL is located at the same locus can be determined in an allelism test.

Although not completely identical to the total amount of sugars, measuring Brix is an approach to indicate the sweetness of products. Degree Brix (° B) is a standard refractometric measure of total soluble solids (mainly sugars in fruits).

The present invention thus provides a pepper plant (*Capsicum annuum* L.) that produces fruits with an increased Brix level, wherein the pepper plant may comprise a QTL which leads to the increased Brix level, wherein the QTL is located on Linkage Group 3 (LG3) and wherein said QTL in the genome of seeds of deposit NCIMB 42139 is linked to at least one marker selected from the group consisting of SEQ ID No:1, SEQ ID No:3, SEQ ID No:5, and SEQ ID No:7 as shown in Table 1. Nomenclature of linkage groups is referred to the consensus chromosome numbers as in Wu et al. (Theor. Appl. Genet. (2009) 118, 1279-1293).

In the genome of plants grown from seeds of the deposit each of the above-mentioned markers is linked to the QTL that causes the trait of the invention which is the trait of producing pepper fruits with increased Brix level. Each of the markers separately is suitable to follow the QTL in breeding but for this purpose also combinations of two or more markers can be used.

The QTL causing the invented trait of increased brix may be identified using the combination of markers SEQ ID No:1, SEQ ID No:3, the combination of markers SEQ ID No:1, SEQ ID No:3, SEQ ID No:5, the combination of markers SEQ ID No:1, SEQ ID No:3, SEQ ID No:5 and SEQ ID No:7, the combination of markers SEQ ID No:1, SEQ ID No:5 and SEQ ID No:7, the combination of markers SEQ ID No:1, SEQ ID No:5, the combination of markers SEQ ID No:1, SEQ ID No:7, the combination of markers SEQ ID No:3, SEQ ID No:5, and SEQ ID No:7, the combination of markers SEQ ID No:3, SEQ ID No:5, the combination of markers SEQ ID No:3, SEQ ID No:7, the combination of markers SEQ ID No:5, SEQ ID No:7.

The QTL is homozygously present in the genome of the deposited material and this material is thus a source of the QTL that can be used to introduce the trait of producing pepper fruits with increased Brix level into other pepper plants. Such plants can be used as a starting point to develop further varieties with the trait of producing pepper fruits with increased Brix level.

Another possible source of the QTL of the invention, the introgression fragment on LG3, is *Capsicum baccatum*. *Capsicum baccatum*, in particular *Capsicum baccatum* var. *pendulum*, may be used as a source of the genomic fragment, the QTL of the invention, to introduce the increased level of Brix trait into *Capsicum annuum* pepper plants. Any *Cap-* sicum annuum pepper plant which may comprise the QTL of the invention, regardless of the source of this QTL, is a plant of the invention. A pepper plant which may comprise the QTL of the invention, wherein this QTL was introduced into this pepper plant from a pepper plant of the invention, for example from a plant grown from seed of deposit NCIMB 42139, is therefore the same or equivalent to a pepper plant which may comprise the QTL of the invention, wherein this QTL was introduced into this pepper plant from a *Capsicum baccatum* plant, in particular a *Capsicum baccatum* var. *pendulum* plant.

In the deposited seeds, the QTL is linked with each of the molecular markers SEQ ID No:1, SEQ ID No:3, SEQ ID No:5, and SEQ ID No:7. These markers may be linked to the QTL, but the presence of at least one of the mentioned markers is not essential in a plant of the invention, as long as the QTL causing the trait is present. The presence of the increased Brix phenotype is a direct indicator that the QTL of the invention is present since the QTL is the genetic information that encodes the novel flavor trait. Thus, a plant of the invention which has the trait of producing pepper fruits with increased Brix level as described herein is still a plant of the invention when the QTL underlying the phenotype is present therein but the markers no longer are.

Markers are sometimes but not always the genetic cause of a trait. Markers may be located in the gene that causes the trait or are genetically linked to it. They are often used as tools to follow the inheritance of the trait. During breeding, the molecular markers that are linked to the genetic determinant in the deposited seeds may be thus used to assist transfer of the novel flavor trait to other plants. A skilled breeder would understand that the transfer of the novel flavor trait into a pepper plant may be monitored by the use of sensory and/or biochemical analysis, or by monitoring and breeding for the presence of molecular markers as described herein (i.e. marker assisted selection), or both. Localization of such markers to specific genomic regions further allows for the use of associated sequences in breeding and for the development of additional linked genetic markers. It will be understood to those skilled in the art that other markers or probes linked to the chromosomal region of the introgression fragment on LG3 as identified herein could be employed to identify plants which may comprise the QTL of the invention. Knowledge of the chromosomal region of the present invention facilitates introgression of the novel flavor trait of the invention from plants which may comprise the QTL of the invention, such as plants grown from the deposited seeds or *Capsicum baccatum* plants, in particular *Capsicum baccatum* var. *pendulum* plants, into other pepper plants. Linkage blocks of various sizes could be transferred within the scope of this invention as long as the chromosomal region confers the novel flavor of the invention. Accordingly, it is emphasized that the present invention may be practiced using any molecular markers that genetically map within the identified region provided that the markers are polymorphic between the parents.

The development of the initial plants with the trait of producing pepper fruits with a sweeter taste as the result of an increased Brix level is described in Example 1. In short, a *Capsicum baccatum* var. *pendulum* accession was used as donor parent for backcrossing (BC) with two cultivated *C. annuum* blocky breeding lines (SM and GNM). Further to these initial crosses, $BC_2S_1$ lines and near-isogenic lines (NILS) were developed that were tested for brix level.

In both the BC2S1 population as in the NILS, the concentration of sugars was measured by enzymatic determination. For the citric and malic acid measurements anion exchange chromatography was used.

The QTL on LG3 that causes pepper plants to produce pepper fruits with an increased Brix level that leads to a sweeter taste can be either homozygously or heterozygously present, both options are covered by this invention.

In Table 1 the nucleotide sequences of the markers SEQ ID NO:1, SEQ ID NO:3, SEQ ID NO:5 and SEQ ID NO:7, which are linked to the QTL of the invention, can be found. In the same Table 1, The nucleotide sequences SEQ ID NO:2, SEQ ID NO:4, SEQ ID NO:6 and SEQ ID NO:8 represent the corresponding wildtype sequences found in plants that do not have the QTL and the markers.

In a preferred embodiment the QTL is homozygously present and the pepper plant produces pepper fruits with an increased Brix level. Plants in which the QTL is heterozygously present are also part of this invention since although they may not or not completely show the phenotype of the invention, such plants are still a source of the QTL and can be used in breeding for developing pepper plants that produce pepper fruits with increased Brix level.

Another aspect of the invention is that pepper fruits produced by a pepper plant having the QTL, have a similar size compared to the pepper fruits of a similar ripening stage of an isogenic pepper plant not having the QTL.

In pepper fruits produced by a pepper plant of the invention the Brix level is increased in order of increasing preference, with at least 0.1 degrees, at least 0.3 degrees, at least 0.5 degrees, at least 0.7 degrees, at least 0.9 degrees, at least 1.1 degrees, at least 1.3 degrees, at least 1.5 degrees, at least 1.7 degrees, at least 1.9 degrees, at least 2.1 degrees, at least 2.3 degrees, at least 2.5 degrees, at least 2.7 degrees, at least 2.9 degrees, at least 3.1 degrees, at least 3.3 degrees, at least 3.5 degrees, at least 3.7 degrees, at least 3.9 degrees, in pepper fruits from a pepper plant which may comprise said QTL compared to pepper fruits of a similar ripening stage from an isogenic pepper plant not comprising said QTL. The QTL that causes the increased Brix may have different effects dependant on the genetic background into which the QTL is introgressed. In some pepper lines, the increase in Brix level caused by the QTL will be relatively higher compared to an isogenic pepper line not having the QTL than in other pepper lines.

The Brix level in pepper fruits produced by plants of the invention is increased in order of increasing preference, with at least 2 percent, at least 4 percent, at least 6 percent, at least 8 percent, at least 10 percent, at least 12 percent, at least 14 percent, at least 16 percent, at least 18 percent, at least 20 percent, at least 22 percent, at least 24 percent, at least 26 percent, at least 28 percent, at least 30 percent, at least 32 percent, at least 34 percent, at least 36 percent, at least 38 percent, at least 40 percent, as compared to pepper fruits of a similar ripening stage from an isogenic pepper plant not comprising said QTL.

Furthermore, the invention relates to a pepper plant of the invention, wherein the increased Brix level in peppers from plants having the QTL as compared to peppers from a pepper plant not comprising said QTL may comprise an increased concentration of at least one of the compounds selected from the group of glucose, fructose, and citrate.

Any of the compounds or any combination of the compounds selected from the group of glucose, fructose, and citrate may contribute to an increase in Brix. In pepper fruits produced by pepper plants which may comprise the QTL of the invention, one or more of said compounds may be similar or even decreased in concentration compared to pepper fruits from plants not having the QTL, the other compound(s) may be increased and therefore the overall Brix level of fruits of said pepper plant may still be increased. In a preferred embodiment, the concentration of all compounds of the group of glucose, fructose and citrate (and thus the Brix level) is increased in pepper fruits of pepper plants which may comprise the QTL of the invention compared to pepper fruits from isogenic pepper plants not which may comprise the QTL.

In a preferred embodiment the QTL is homozygously present and the pepper plant produces peppers with increased Brix level.

Another aspect of the invention relates to a pepper plant producing peppers with increased Brix level, wherein the increased Brix level is caused by a QTL on LG3, which pepper plant is obtainable by or obtained by crossing a first pepper plant having the QTL, with a second pepper plant that may or may not have the QTL, or by introgression of the QTL into the first pepper plant from the second pepper plant, and selecting in any progeny generation of the cross the pepper fruits which have the increased Brix level and/or increased concentrations of glucose, fructose and citrate and wherein the QTL is as found in the deposit and/or linked to at least one of the molecular markers selected from the group of SEQ ID NO:1, SEQ ID NO:3, SEQ ID NO:5 and SEQ ID NO:7.

The pepper plants according to the invention may grow the following fruit types: sweet pepper including pepper, bell pepper, big rectangular pepper, conical pepper, long conical pepper or blocky-type pepper or snack or dolma (=mini blocky). The fruits of the pepper plants according to the invention at maturity may be green, yellow, orange, red, ivory, brown, or purple.

In one embodiment, the pepper plant of the invention is a representative of *Capsicum annuum*, or any hybrid combination of *Capsicum annuum* with other closely related *Capsicum* species.

The invention relates also to seed of pepper plants of the invention and to other parts of the plant that are suitable for sexual reproduction. Such plant parts can be selected from the group consisting of microspores, pollen, ovaries, ovules, embryo sacs and egg cells.

Additionally, the invention also relates to parts of the pepper plants of the invention that are suitable for vegetative reproduction, for example tissue culture, cuttings, roots, stems, cells and protoplasts. Tissue culture can be grown from leaves, pollen embryos, cotyledon, hypocotyls, meristematic cells, roots, anthers, flowers, seeds and stems.

Another aspect of the invention relates to progeny of pepper plant of the invention or progeny of pepper plants grown from seeds derived from pepper plants of the invention wherein the progeny has the QTL of the invention. Such progeny can be produced by sexual or vegetative reproduction of a plant of the invention or a progeny plant thereof. Such progeny has the same characteristics as claimed for the pepper plants of the invention. The progeny carries the QTL on LG3 as found in the plant of the invention and as present in plants grown from seed of which a representative sample was deposited at the NCIMB under number NCIMB 42139. In addition to this, the plant may be modified in one or more other characteristics. Such additional modifications are for example effected by crossing and selecting, mutagenesis or by transformation with a transgene. In a preferred embodiment the QTL of the invention is present in a homozygous state in such progeny.

The invention also relates to propagation material derived from a pepper plant of the invention or from pepper seeds derived from pepper plants of the invention, wherein the propagation material may comprise the QTL, and wherein the QTL is preferably present in a homozygous state.

In addition the invention relates to propagation material capable of growing into a pepper plant of the invention, wherein the propagation material may comprise the QTL, and wherein the QTL is preferably present in a homozygous state.

The propagation material can be selected from the group consisting of callus, microspores, pollen, ovaries, ovules, embryos, embryo sacs, egg cells, cuttings, roots, stems, cells, protoplasts, leaves, cotyledons, hypocotyls, meristematic cells, roots, root tips, microspores, anthers, flowers, seeds and stems or parts or tissue culture thereof.

As used herein the word "progeny" is intended to mean the offspring or the first and all further descendants from a cross with a plant of the invention that shows the trait of the invention and carries the QTL of the invention underlying the trait. Progeny of the invention may comprise descendants of any cross with a plant of the invention that carries the QTL causing the trait of the invention. Such progeny is for example obtainable by crossing a first pepper plant with a second pepper plant, wherein one of the plants was grown from seeds of which a representative sample was deposited under accession number NCIMB 42139, but may also be the progeny of any other pepper plant carrying the QTL of the invention as present in NCIMB 42139.

The invention furthermore, relates to hybrid seeds and to a method of producing hybrid seed which may comprise crossing a first parent plant with a second parent plant and harvesting the resulting hybrid seed. In case the trait is recessive, both parent plants need to be homozygous for the increased Brix level QTL in order for the hybrid to have the trait of increased Brix level. In case the trait is intermediate, both parent plants need to be homozygous for the increased Brix level QTL in order for the hybrid seeds to grow into plants that can express the full potential of the trait of the invention. If only one of the parent pepper plants is homozygous for the QTL and the other parent is heterozygous, only one half of the hybrid seed will grow into pepper plants that show the full potential of the trait of the invention. The other half of the hybrid seed will still carry the QTL of the invention, but plants grown from this hybrid seed will have peppers with some increase in Brix level, more than without the QTL of the invention, but less than pepper plants being homozygous for the QTL of the invention. If the trait is dominant it obviously does not matter whether one or both parents is/are homozygous for the QTL. In all scenarios, the parent plants need not necessarily to be uniform for other traits.

In one embodiment, the invention relates to pepper plants that carry the pepper fruits with increased Brix level trait of the invention and having acquired said trait by introduction of the genetic information or QTL that is responsible for the trait from a suitable source, either by conventional breeding, or genetic modification, in particular by cisgenesis or transgenesis. Cisgenesis is genetic modification of plants with a natural gene, coding for a (agricultural) trait, from the crop plant itself or from a sexually compatible donor plant. Transgenesis is genetic modification of a plant with a gene from a non-crossable species or a synthetic gene.

In one embodiment, the source from which the genetic information leading to the trait of pepper fruits with increased Brix level is acquired are plants grown from the deposited seeds or sexual or vegetative descendants therefrom.

The invention further relates to cells of the pepper plants that show the trait of the invention, pepper fruits with increased Brix level. Each cell of such pepper plants carries in its genome the genetic information that leads to phenotypic expression of said trait of producing pepper fruits with increased Brix level. The cell may be an individual cell or may be part of a pepper plant or pepper plant part.

Another aspect of the invention relates to fruits of the pepper plant, commonly also known as peppers, or parts thereof, from a pepper plant of the invention, which may comprise the QTL and showing increased Brix level.

In addition, the invention also relates to any food products or processed food products made of pepper fruits from the invention. Examples of food products that may comprise pepper in raw, cooked or otherwise processed form include powders, soups, sauces, salsas, pastas, condiments, pastries, sweets and salads.

The invention also relates to the use of a pepper plant from the invention as germplasm in a breeding program for the development of pepper plants which may comprise a QTL that leads to increased Brix level in pepper fruits. The germplasm is constituted by all inherited characteristics of an organism and according to the invention encompasses at least the trait of producing pepper fruits with increased Brix level.

Furthermore, also part of the invention is the isolated nucleic acid or a part thereof which is causative of an increased Brix level in pepper fruits, in which the nucleic acid originates from a QTL on LG3 of a *Capsicum baccatum* plant or a pepper plant as in claim 1 or 2 and is optionally linked to at least one molecular marker selected from the group of SEQ ID NO:1, SEQ ID NO:3, SEQ ID NO:5 and SEQ ID NO:7 and/or is as present in seeds of the deposit of NCIMB 42139.

A person skilled in the art would be able to isolate the nucleic acid causing the trait of the invention or a part thereof from the genome of a pepper plant of the invention, and use it to create new molecular markers that are linked with the QTL and with the trait of the invention.

Also part of the invention is the use of molecular markers to identify the QTL located on Linkage Group LG3 in a pepper plant producing pepper fruits with increased Brix level, wherein the marker is selected from the group consisting of SEQ ID No:1, SEQ ID No:3, SEQ ID No:5, SEQ ID No:7 and/or to identify or develop other pepper plants with an increased Brix level and/or to identify or develop other markers linked to the QTL. Genotyping a population of plants segregating for the Brix level trait of the invention can be done using at least one molecular marker set selected from the group consisting of SEQ ID No:1 plus SEQ ID No:2, SEQ ID NO:3 plus SEQ ID NO:4, SEQ ID NO:5 plus SEQ ID NO:6 and SEQ ID NO:7 plus SEQ ID NO:8.

The current molecular markers linked to the QTL of the invention as mentioned in this application can be a starting point to develop other molecular markers that will be linked to the QTL that causes plants to produce pepper fruits with increased Brix level. The original molecular markers might or might not be any more linked to the QTL, but the pepper plants are still considered to be part of the invention as long as the QTL is present.

The invention further relates to a cell of a pepper plant of the invention, which cell may comprise the QTL which confers the trait of producing pepper fruits with increased Brix level, wherein said QTL is obtainable from the genome of a *Capsicum baccatum* plant or a pepper plant, in particular a pepper plant grown from seeds of which a representative sample was deposited with the NCIMB under accession number NCIMB 42139. Said pepper plant of the invention is obtainable by crossing a pepper plant with a second pepper plant, in particular a pepper plant grown from seed as deposited under accession number NCIMB 42139, and selecting for a pepper plant that has the trait of the invention. The said cell thus may comprise the genetic information which is substantially identical, preferably completely identical to the genetic information encoding the said trait of producing pepper fruits with increased Brix level of the pepper plant grown from seeds of which a representative sample was deposited under NCIMB accession number 42139, more in particular the QTL described herein. Preferably, the cell of the invention is a part of a plant or plant part, but the cell may also be in isolated form.

In one embodiment, the invention relates to the use of seeds with NCIMB accession number NCIMB 42139, for transferring the QTL of the invention, which confers the trait of the invention, into another pepper plant.

In another embodiment, the invention relates to the use of a pepper plant, which plant carries the QTL that confers the increased level of Brix trait, which QTL is obtainable from a *Capsicum baccatum* or pepper plant carrying the QTL of the invention, in particular a pepper plant grown from seed of which a representative sample was deposited under accession number NCIMB 42139, as a crop.

The invention also relates to the use of a pepper plant, which carries the QTL that confers the increased level of Brix trait of the invention, which QTL is obtainable from a *Capsicum baccatum* or pepper plant carrying the QTL of the invention, in particular a pepper plant grown from seed of which a representative sample was deposited under accession number NCIMB 42139, as a source of seed.

In yet another embodiment, the invention relates to the use of a pepper plant, which carries the QTL that confers the increased level of Brix trait, which QTL is obtainable from a *Capsicum baccatum* or pepper plant carrying the QTL of the invention, in particular a pepper plant grown from seed of which a representative sample was deposited under accession number NCIMB 42139, as a source of propagating material.

Further, the invention relates to the use of a pepper plant, which carries the QTL that confers the increased level of Brix trait, which QTL is obtainable from a *Capsicum baccatum* or pepper plant carrying the QTL of the invention, in particular a pepper plant grown from seed of which a representative sample was deposited under accession number NCIMB 42139, for consumption.

In another embodiment, the invention relates to the use of a *Capsicum baccatum* plant or a pepper plant, which carries the QTL which confers an increased level of Brix trait as available from seeds with NCIMB accession number NCIMB 42139, for conferring the QTL that leads to the trait of the invention to a pepper plant.

In yet another embodiment, the invention relates to the use of a pepper plant, as a recipient of the QTL as present in and available from a *Capsicum baccatum* plant or a pepper plant carrying the QTL of the invention, in particular pepper plants grown from seeds registered under NCIMB accession number NCIMB 42139.

The current invention also relates to a pepper fruit, or parts thereof, harvested from a pepper plant of the invention, producing fruits with increased Brix level and which may comprise the QTL as defined herein. Naturally this also relates to any food product or processed food product made of said pepper fruit.

The processed pepper fruit may also be included in another food product, such as sauce, pie, soup or a dried or fresh pasta product, such as ravioli, tortellini, cannelloni etc. Such food product will usually be pre-packed and is intended for sale in a supermarket. The invention thus also relates to the use of pepper fruits harvested from a pepper plant of the invention, or parts thereof, in the preparation of food products, in particular sauces, salads, pies, soups and pastas.

In one aspect the invention relates to a method for production of a pepper plant which has the trait of increased Brix level, which may comprise
 a) crossing a pepper plant which may comprise a QTL that leads to the trait, with another pepper plant;
 b) selfing the resulting F1 for obtaining F2 plants;
 c) selecting F2 pepper plants that have the trait;
 d) optionally performing one or more additional rounds of selfing or crossing, and subsequently selecting plants which may comprise the QTL of the invention and producing fruits with increased Brix level.

It is clear that the parent that provides the QTL that confers the trait of the invention is not necessarily a plant grown directly from the deposited seeds. The parent may also be a progeny plant from the deposited seed, obtained by for example selfing or crossing, or a progeny plant from seeds that are identified to have the trait of the invention by other means.

The invention additionally provides a method of introducing another desired trait into a pepper plant which has the trait of producing pepper fruits with increased Brix level, which may comprise:
 a) crossing a pepper plant that has the trait of producing pepper fruits with increased Brix level, representative seeds of which were deposited under deposit number NCIMB 42139, with a second pepper plant that may comprise a desired trait to produce F1 progeny;
 b) selecting in the F1 progeny plants that may comprise said trait of producing pepper fruits with increased Brix level and the desired trait;
 c) crossing the selected F1 progeny plants with either parent, to produce backcross progeny;
 d) selecting backcross progeny plants which may comprise the desired trait and the trait of producing pepper fruits with increased Brix level; and
 e) optionally repeating steps c) and d) one or more times in succession to produce selected fourth or higher backcross progeny that may comprise the desired trait and the trait of producing pepper fruits with increased Brix level. The invention includes a pepper plant produced by this method.

In one embodiment selection for plants having the trait of producing pepper fruits with increased Brix level is done in the F1 or any further generation by using any or any combination of the markers according to SEQ ID No:1, SEQ ID No:3, SEQ ID No:5, and SEQ ID No:7. In another aspect, selection for the trait of the invention is started in the F2 of a cross or alternatively of a backcross. Selection of plants in the F2 can be done phenotypically as well as by using the said marker(s) which directly or indirectly detect(s) the QTL underlying the trait.

In one embodiment selection for plants having the trait of producing pepper fruits with increased Brix level is started in the F3 or a later generation.

In one embodiment the plant which may comprise the QTL is a plant of an inbred line, a hybrid, a doubled haploid, or of a segregating population.

The invention further provides a method for the production of a pepper plant having the trait of producing pepper fruits with increased Brix level by using a doubled haploid generation technique to generate a doubled haploid line which may comprise said trait.

The invention also relates to a method for the production of a pepper plant having the trait of producing pepper fruits with increased Brix level by using a seed that may comprise a QTL in its genome that leads to the trait of producing pepper fruits with increased Brix level for growing the said pepper plant. The seeds are suitably seeds of which a representative sample was deposited with the NCIMB under deposit number NCIMB 42139.

The invention also relates to a method for seed production which may comprise growing pepper plants from seeds of which a representative sample was deposited with the NCIMB under deposit number NCIMB 42139, allowing the plants to produce seeds, and harvesting those seeds. Production of the seeds is suitably done by crossing or selfing.

In one embodiment, the invention relates to a method for the production of a pepper plant having the trait of producing pepper fruits with increased Brix level by using tissue culture.

The invention furthermore relates to a method for the production of a pepper plant having the trait of producing pepper fruits with increased Brix level by using vegetative reproduction.

In one embodiment, the invention relates to a method for the production of a pepper plant having the trait of producing pepper fruits with increased Brix level by using a method for genetic modification to introgress the QTL causing the said trait into the pepper plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for the development of pepper plants that have the trait of producing pepper fruits with increased Brix level wherein germplasm which may comprise the QTL causing said trait is used. The germplasm is constituted by all inherited characteristics of an organism and according to the invention encompasses at least the trait of producing pepper fruits with increased Brix also known as the trait of the invention. Representative seed of said plant which may comprise the QTL and being representative for the germplasm was deposited with the NCIMB under deposit number NCIMB 42139.

In a further embodiment the invention relates to a method for the production of a pepper plant having the trait of producing pepper fruits with increased Brix level wherein progeny or propagation material of a plant which may comprise the QTL or genetic determinant conferring said trait is used as a source to introgress the said trait into another pepper plant. Representative seed of said plant which may comprise the QTL was deposited with the NCIMB under deposit number NCIMB 42139.

The invention provides preferably a pepper plant having the trait of producing pepper fruits with increased Brix level, which plant is obtainable by any of the methods herein described and/or familiar to the skilled person.

In the absence of molecular markers, or in the instance that recombination between the QTL and the marker has taken place so that the marker is not predictive anymore, equivalence of QTLs can be determined by an allelism test. To perform an allelism test, a tester plant which is homozygous for the known QTL or genetic determinant of the invention is crossed with material to be tested that is also homozygous for its QTL. This latter plant is referred to as the donor plant. The donor plant to be tested should be or should be made homozygous for the genetic determinant(s) to be tested. The skilled person knows how to obtain a plant that is homozygous for the QTL or genetic determinant to be tested. When no segregation for the trait to be observed is present in the F2 resulting from the cross, the QTLs or genetic determinants have been proven to be equivalent or the same.

When more than one gene may be responsible for a certain trait, and an allelism test is done to determine equivalence, the skilled person doing the test has to make sure that all relevant genes are present homozygously in the material to be tested, for the test to work properly.

Furthermore, the invention relates to an increased Brix gene that leads to a pepper plant having the increased Brix trait of the invention, and which gene is as present in the genome of plants of which a representative sample was deposited with the NCIMB under deposit number NCIMB 42139. The skilled breeder knows how to use such plant as a source of the increased Brix gene for introgressing the gene into a plant.

The invention also relates to the use of the QTL that leads to a pepper plant producing fruits having the trait of increased Brix, for producing a plant, in particular a pepper plant, which has the trait of increased Brix, which QTL is as present in the genome of plants of which a representative sample was deposited under deposit number NCIMB 42139.

According to another aspect thereof the invention relates to a non-naturally occurring plant producing fruits having an increased Brix, and which increased Brix is the result of the presence in the genome of the plant of the QTL which is as present in the genome of plants of which a representative sample was deposited under deposit accession number 42139. The non-naturally occurring plant is in particular a mutant plant.

"Introgression" as used in this application is intended to mean introduction of a trait into a plant not carrying the trait by means of crossing and selecting. Introgression may comprise multiple rounds of crossing and selecting depending on whether the trait is dominant, intermediate or recessive.

The word "trait" in the context of this application refers to the phenotype of the plant. In particular, the word "trait" refers to the trait of the invention, more in particular to the trait of pepper fruits with increased Brix level.

The term "QTL" (i.e. "quantitative trait locus") is used for the genetic information in the genome of the plant that causes the trait of the invention. When a plant shows the trait of the invention, its genome may comprise the QTL causing the trait of the invention. The plant thus has the QTL of the invention. In the present invention the QTL is an introgression from *C. baccatum* on Linkage Group 3 (LG3).

The term 'nucleic acid' is used for a macromolecule, a DNA or RNA molecule, containing the genetic information that causes the trait of the invention. When a plant shows the phenotypic trait of the invention, its genome may comprise the nucleic acid causing that trait. The plant thus has the nucleic acid of the invention. In the present invention the nucleic acid is part of the QTL introgressed from *C. baccatum* on Linkage Group 3 (LG3).

Marker Information

TABLE 1

Molecular SNP markers

| marker name | LG | position (cM) | Sequence marker |
|---|---|---|---|
| SEQ ID No: 1 | 3 | 0.00 | TTAAACTATCCTTTTCCAATCACCAC ATGGCCAGGCTTCGACTTGCTAAAAG CTCTTTTCAGCATTTGACCCTCCGCA GAGAGAGCGGTTGAAAGCTTGTAAAC ATGAACAAG |
| SEQ ID No: 2 | 3 | 0.0 | TTAAACTATCCTTTTCCAATCACCAC ATGACAGGCTTCGACTTGCTAAAAG CTCTTTTCAGCATTTGACCCTCCGCA GAGAGAGCGGTTGAAAGCTTGTAAAC ATGAACAAG |
| SEQ ID No: 3 | 3 | 2.74 | GACTTGTTTTGTCTGGGATTGAATGT TTTTTATTGTTGTAGTAGTAGCAGAA GCAAAAAATGTTGATGTAAATTATGA AATATTACTGCTAATATTTGTG |
| SEQ ID No: 4 | 3 | 2.74 | GACTTGTTTTGTCTGGGATTGAATGT TTTTTATTGTTGTAGTAGTAGCAGAA GCGAAAAATGTTGATGTAAATTATGA AATATTACTGCTAATATTTGTG |
| SEQ ID No: 5 | 3 | 3.88 | TCAGCCAGTACTAGTTCTGCTCTCCA AACCTGGTTAGGAAAAAAAACAGCTA CATGAATAGTATATAATGCACTAAAA AMYTCAGATAGCTAAACGAGAACGAA CAATAGTCACTACTGGGAYWSRSAAM MVDTDTTWACACTAAATGGAAAATAC A |
| SEQ ID No: 6 | 3 | 3.88 | TCAGCCAGTACTAGTTCTGCTCTCCA AACCTGGTTAGGAAAAAAAACAGCTA CATGAATAGTATATAATGCACTAAAA AMYTCAGATAGCTAAATGAGAACGAA CAATAGTCACTACTGGGAYWSRSAAM MVDTDTTWACACTAAATGGAAAATAC A |
| SEQ ID No: 7 | 3 | 19.57 | CTGCACCAGCTCTGCTTGCACTAAAA CAGAAACGACTGACGTTTACCTGGCT TGATGGGGAAGCACAGAAAGTGAGCA CCTCTCTTCAAATGTTTGCATTCCTT TGGTTAA |
| SEQ ID No: 8 | 3 | 19.57 | CTGCACCAGCTCTGCTTGCACTAAAA CAGAAACGACTGACGTTTACCTGGCT TGATGGGGAAGCACAGAAAGTGAGCA TTCTCTTCAAATGTTTGCATTCCTT TGGTTAA |

The nucleotides in bold script indicate the SNPs.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Development of a Pepper Plant with an Increased Brix Level

The *Capsicum baccatum* var. *pendulum* accession PEN45 was used as donor parent for backcrossing (BC) with three cultivated *Capsicum annuum* blocky breeding lines (MT, SM and GNM). Because of difficulties in interspecific crossing, a multi-parent BC2 population, consisting of three sub-populations, was generated for linkage map development. The largest PEN45 BC2 sub-population out of the three, with the blocky parents SM and GNM in its pedigree, was chosen to study fruit characteristics in more detail. In this population 34 of the in total 54 BC2 plants gave sufficient inbred seeds to grow BC2S1 lines. In 2009 the 34 BC2S1 lines were grown in plots of 5-9 plants with, if possible, 2 repetitions (possible for 23 BC2S1 lines) in a randomized block design. Plants were grown in soil in a greenhouse in De Lier, The Netherlands, with 2 stems per plant and with 2.5 plants/m².

Due to the generation of the material and the presence of two different breeding lines (SM and GNM) in their pedigree, the lines were still segregating for several traits. To grow the BC2S1 lines as uniform as possible, plants were pre-selected with a marker based on the Pun1 locus for selection of non-pungent plants and with a marker based on the CCS gene (capsanthin-capsorubin synthase) to select non-red (i.e. yellow or orange) plants. To compensate for selection against Pun1 or CCS linked PEN45 fragments with potentially interesting characteristics, two and five BC2S1 lines (out of the 34 lines) were used to select plants with homozygous pungent orange fruits and homozygous non-pungent red fruits, respectively. These plants were also grown in 2 repetitions with plots of 5 plants. Genotypes SM, GNM and PEN45 were grown as controls in four repetitions.

At the time of maturation of the first fruits the BC2S1 plots were made phenotypically more uniform by removing the most aberrant, mainly sterile, plants from the plots. In total 25 of the BC2S1 lines were uniform for orange color, the other 9 lines were segregating for plants with either orange or yellow fruits. In the end 250 BC2S1 plants remained in 69 plots (1-6 plants) and were used for QTL mapping, of which 160 orange, 61 yellow and 29 red fruited plants.

Three different BC2S1 plants, from three different BC2 plants, were used to develop near-isogenic lines (NILs) by one generation of backcrossing with GNM followed by two selfing steps. A NIL population consists of genetically homogeneous lines, which only differ from each other by the presence of (different) single or a small number of introgression fragment(s) from a donor parent. In this case, the donor parent is the accession PEN45, the *C. baccatum* parent.

Each generation (i.e. both backcrossing and selfing steps) was genotyped with SNPs flanking the original BC2S1 introgressions to obtain BC3S2 lines with a limited number of introgressions in a GNM genetic background. In 2011 23 NILs and the recurrent parent (GNM) were grown in three repetitions with 5 plants per plot in a completely randomized setup. Plants were grown under similar conditions as the BC2S1 lines in a greenhouse, this time in autumn and on rockwool.

Example 2

Sampling of Pepper Fruits for Biochemical Analysis

Ripe fruits (95-100% colored) from the second fruit set were used for biochemical measurements. Fruits were stored after harvesting in a climate room at 20° C. with 80% relative humidity for 3-4 days to optimize ripening. This is a procedure to mimic the Dutch commercial system. During the day of the sensory evaluations, fruits were washed with cold running tap water, dried with a clean towel, cut (top and bottom parts were discarded) in 1-2 cm pieces, mixed and seeds were removed. Half of the fruit pieces from each sample were immediately frozen in liquid nitrogen, ground in an electric mill and stored at −80° C., while the other half was used for flavor evaluation.

Fruits of the BC2S1 plants were harvested per plot and in case of plots segregating for plants with either orange or yellow fruits, the two colors were bulked separately. 56 BC2S1 plots (37 orange, 15 yellow and 4 red) gave sufficient fruits to make representative fruit samples of 5-8 fruits for sensory evaluation. In addition 32 samples were made of plots and/or individual plants that did not give enough fruits for sensory evaluation or that were pungent.

In the NIL experiment, 20 NILs and GNM gave sufficient fruits and were evaluated as bulks per plot.

Example 3

Brix Level and Non-volatile Compounds Analysis of Pepper Fruits

In both experiments, in the $BC_2S_1$ and the NILs, the concentration of sugars (fructose, glucose and sucrose) was measured by enzymatic determination (Velterop J S and Vos F (2001) A rapid and inexpensive microplate assay for the enzymatic determination of glucose, fructose, sucrose, L-malate and citrate in tomato (*lycopersicon esculentum*) extracts and in orange juice. Phytochemical analysis 12:299-304.). In both experiments the sucrose concentrations turned out to be under the detection limit (0.3 g/100 g fresh weight) of the enzymatic determination method. Anion exchange chromatography was used for citric and malic acid determination based on standard protocols (Dionex Corporation, Sunnyvale, Calif.; http://www.dionex.com/Application Note 143 "Determination of Organic Acids in Fruit Juices"). Sugar and acid measurements were completed by pH and total soluble solids (Brix) determination. Clear supernatants of shortly centrifuged samples were used for refractive index measurement of total soluble solids content (TSS; ° Brix). Degrees Brix (symbol ° Bx) is the sugar content of an aqueous solution. One degree Brix is 1 gram of sucrose in 100 grams of solution and represents the strength of the solution as percentage by weight (% w/w). If the solution contains dissolved solids other than pure sucrose, then the Brix only approximates the total soluble solids content.

The QTL analysis using the non-volatile data was performed as described in Example 4.

In the NILs non-volatile effects were found, relating to a *C. baccatum* introgression on LG3 of 0-19.6 cM. Brix and the concentration of glucose, fructose and citrate were significantly increased in the NIL having this fragment, while the malate concentration was not significantly affected.

The LG3 introgression gave a strong effect, resulting in a Brix level increase of 1.76 degrees in the plants from the NIL which may comprise the QTL on LG3 compared to all other NILs lacking this fragment and an increase of 2.47 degrees compared to the recurrent parent GNM (Table 2). Most interesting, this effect seemed to be unrelated to fruit size, as the fruits of NIL51 had a similar size (8×7 cm; length×width) as the fruits of GNM (8×8 cm).

Example 4

Fruit Size and Shape Analysis of Pepper Fruits

A fruit description of all 250 $BC_2S_1$ plants and controls was made in the first week of July 2009. The shape of the fruits (conical or blocky) was recorded and average length and maximum width (cm; length1 and width1) were estimated by eye from all full grown (ripe and unripe) fruits hanging on the plant, by an experienced breeder using 0.5 cm intervals. Subsequently the mature fruits were harvested and pooled per plot (76 samples excluding controls). Average weight (gram), length and width (cm; length$^2$ and width$^2$) were measured on 5 representative fruits. From the NILS the average length and maximum width were estimated by eye from all full grown (ripe and unripe) fruits hanging on the plant, by an experienced breeder using 0.5 cm intervals. Fruits of the NILS, having different introgressions were compared with the fruits from the parent plants to check for negative effects of the introgressions. As mentioned in Example 3, the introgression/QTL on LG3 that causes the increase of Brix in pepper fruits, does not seem to have a negative influence on the shape or size of the fruits.

Example 5

QM Analysis/Identification of the QTL

In total 250 BC2S1 plants from the *C. baccatum* var. *pendulum* BC2 sub-population having the blocky parents SM and GNM in its pedigree, were genotyped with 239 SNPs that were polymorphic in *C. baccatum* var. *pendulum* versus SM and GNM. The Interval Mapping method within the program MapQTL 6 (Van Ooijen (2009) MapQTL6; software for the mapping of quantitative trait loci in experimental populations of diploid species. Kyazma B V, Wageningen, The Netherlands) was used for QTL identification in the BC2S1 experiment. Graphics were produced by MapChart software (Voorrips, Journal of Heredity (2002) 93, 77-78). Non-volatiles (88 plots/plants) and fruit size and shape characteristics (250 plants) were analyzed in separate sessions. A permutation test was applied to each data set (1000 permutations) to determine the LOD (Logarithm of odds) thresholds. A genome wide (GW) LOD threshold of 2.7 was used for QTL significance (p<0.05). The chromosomal locations with the highest GW LOD scores were considered to be the most likely positions of a QTL. Linkage groups were named and oriented based on the chromosome numbering and orientation of Wu et al. (Theor. Appl. Genet. (2009) 118, 1279-1293). The NIL experiment was analyzed using the non-parametric Kruskal-Wallis test within MapQTL 6 to identify markers that showed significant (p<0.05) trait associations. The analyses in both experiments were performed with log 2 transformed metabolite data. The analyses of the non-volatile compounds are described in Example 3.

The *C. baccatum* introgression at the top of LG3 (see FIG. 1) in NIL51 resulted in an increase in Brix level and underlying levels of soluble solids, glucose, fructose and citrate. (see Example 3) (see Table 2).

TABLE 2

The effect of the LG3 QTL on level of Brix, sugar and acid in the NILs and GNM

| Trait | Signif. | LG3 | | | GNM |
|---|---|---|---|---|---|
| | | mA | mB | A/B | |
| Brix | 0.005 | 7.94 | 9.70 | 60/3 | 7.23 |
| Glucose | 0.005 | 2.87 | 3.71 | 60/3 | 2.42 |
| Fructose | 0.01 | 3.07 | 3.72 | 60/3 | 2.64 |
| Citrate | 0.005 | 323.40 | 513.43 | 60/3 | 303.56 |
| Malate | ns | 24.48 | 19.79 | 60/3 | 23.52 |

Means (m) and genotype distribution (A/B) are given.
ns = not significant.
GNM is one of the original parents, not having the QTL on LG3.

The invention is further described by the following numbered paragraphs:

1. A pepper plant (*Capsicum annuum*) that produces fruits with an increased Brix level, wherein the pepper plant comprises a QTL, which when present leads to pepper fruits with increased Brix level, and wherein said QTL is similar to, or in particular the same as the QTL present in the genome of plants grown from seed which was deposited at the NCIMB under NCIMB number 42139, and wherein said QTL is linked to at least one marker selected from the group of SEQ ID NO:1, SEQ ID NO:3, SEQ ID NO:5, and SEQ ID NO:7 and wherein the QTL is preferably homozygously present.

2. A pepper plant of paragraph 1, wherein the QTL is the same as a QTL that is present in the genome of plants grown from seeds of deposit NCIMB 42139 and is linked therein to markers SEQ ID No:1, SEQ ID No:3, SEQ ID No:5, and SEQ ID No:7.

3. A pepper plant of paragraph 1 or 2, wherein the QTL is located on LG3 and wherein the QTL is as present in or obtainable from the genome of *Capsicum baccatum* plants or pepper plants grown from seed which was deposited at the NCIMB under NCIMB number 42139 and wherein the QTL is preferably homozygously present.

4. A pepper plant of any one of the paragraphs 1-3, wherein the pepper fruits produced by the pepper plant having the QTL have a similar size compared to the pepper fruits of a similar ripening stage of an isogenic pepper plant not having the QTL.

5. A pepper plant of any one of the paragraphs 1-4, wherein the Brix level in the pepper fruits comprising the QTL is increased in order of increasing preference, by at least 0.1 degrees, at least 0.3 degrees, at least 0.5 degrees, at least 0.7 degrees, at least 0.9 degrees, at least 1.1 degrees, at least 1.3 degrees, at least 1.5 degrees, at least 1.7 degrees, at least 1.9 degrees, at least 2.1 degrees, at least 2.3 degrees, at least 2.5, at least 2.7, at least 2.9, at least 3.1, at least 3.3 at least 3.5, at least 3.7, at least 3.9 degrees compared to the Brix level in pepper fruits from an isogenic pepper plant not comprising said QTL.

6. A pepper plant of any one of the paragraphs 1-5, wherein the increased Brix level of the pepper fruits comprises an increased concentration of at least one of the compounds selected from the group of glucose, fructose, and citrate in pepper fruits as compared to compounds in pepper fruits from a pepper plant not comprising said QTL.

7. Seed of a pepper plant of any one of the paragraphs 1-6, comprising the QTL as defined in any one of the paragraphs 1-3, and wherein the QTL is preferably homozygously present.

8. Seed of a pepper plant capable of growing into a pepper plant of any of the paragraphs 1-6, comprising the QTL as defined in any one of the paragraphs 1-3, and wherein the QTL is preferably homozygously present.

9. Progeny of a pepper plant of any one of the paragraphs 1-6 or progeny of pepper plants grown from seed of paragraph 7 or 8, wherein the progeny of the plant comprises the QTL, wherein the QTL is preferably present in a homozygous state.

10. Propagation material derived from a pepper plant of any one of the paragraphs 1 to 6 or 9 or from pepper seeds of paragraph 7 or 8 or from plants grown from said seeds, wherein the propagation material comprises the QTL as defined in any one of the paragraphs 1-3 and wherein the QTL is preferably present in a homozygous state.

11. Propagation material capable of growing into a pepper plant of any one of the paragraphs 1 to 6.

12. Propagation material of paragraph 9-10, wherein the propagation material is selected from the group consisting of callus, microspores, pollen, ovaries, ovules, embryos, embryo sacs, egg cells, cuttings, roots, stems, cells, protoplasts, leaves, cotyledons, hypocotyls, meristematic cells, roots, root tips, microspores, anthers, flowers, seeds and stems or parts or tissue culture thereof.

13. A pepper fruit, or parts thereof, from a pepper plant of any one of the paragraphs 1 to 6, or 9 or grown from seeds of paragraph 7 or paragraph 8 comprising the QTL as defined in any one of the paragraphs 1-3.

14. A food product or a processed food product comprising a pepper fruit or a part thereof of paragraph 13.

15. The use of a pepper plant of any one of the paragraphs 1-6 as germplasm in a breeding program for the development of pepper plants producing pepper fruits with an increased Brix level and/or an increased concentration of any of the compounds selected from the group of glucose, fructose and citrate.

16. A nucleic acid or a part thereof, optionally in isolated form, which causes an increased Brix level in pepper fruits, which nucleic acid originates from a QTL on Linkage group LG3 of a *Capsicum baccatum* plant or a pepper plant as in any one of the paragraphs 1-3, and which is linked thereon to at least one molecular marker selected from the group of SEQ ID NO:1, SEQ ID NO:3, SEQ ID NO:5, and SEQ ID NO:7.

17. Use of a molecular marker to identify the QTL located on Linkage Group LG3 in a pepper plant as in any one of the paragraphs 1-3, and/or to identify or develop other pepper plants with an increased concentration of Brix level as in paragraph 4 or paragraph 5 and/or to identify or develop other markers linked to the QTL on LG3 in any one of the paragraphs 1-3.

\* \* \*

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A *Capsicum annuum* plant that produces a fruit with an increased Brix level, wherein the plant is a sweet pepper plant and comprises a QTL from *Capsicum baccatum* var. *pendulum*, which when present leads to a pepper fruit with an increased Brix level compared to the Brix level in a pepper fruit from an isogenic *Capsicum annuum* plant not comprising said QTL, wherein said QTL is present in the genome of plants grown from seed which was deposited at the NCIMB under accession number 42139;

and wherein said *Capsicum annuum* plant comprising said QTL from *Capsicum baccatum* also comprises SEQ ID NO:1, SEQ ID NO:3, SEQ ID NO:5, and SEQ ID NO:7.

2. The plant of claim 1, wherein the QTL is homozygously present.

3. The plant of claim 1, wherein the pepper fruit produced by the pepper plant having the QTL has a similar size compared to the pepper fruit of a similar ripening stage of an isogenic pepper plant not having the QTL.

4. The plant of claim 1, wherein the Brix level in the pepper fruit comprising the QTL is increased by at least 0.1 degrees, at least 0.3 degrees, at least 0.5 degrees, at least 0.7 degrees, at least 0.9 degrees, at least 1.1 degrees, at least 1.3 degrees, at least 1.5 degrees, at least 1.7 degrees, at least 1.9 degrees, at least 2.1 degrees, at least 2.3 degrees, at least 2.5 degrees, at least 2.7 degrees, at least 2.9 degrees, at least 3.1 degrees, at least 3.3 degrees, at least 3.5 degrees, at least 3.7 degrees, or at least 3.9 degrees, compared to the Brix level in a pepper fruit from an isogenic pepper plant not comprising said QTL.

5. The plant of claim 1, wherein the increased Brix level of the pepper fruit comprises an increased concentration of at least one of the compounds selected from the group of glucose, fructose, and citrate in a pepper fruit as compared to at least one of the compounds in a pepper fruit from a pepper plant not comprising said QTL.

6. A seed of the plant of claim 1, wherein the seed comprises the QTL as defined in claim 1.

7. The seed of claim 6, wherein the QTL is homozygously present.

8. A seed of a plant capable of growing into the plant of claim 1, wherein the seed comprises the QTL as defined in claim 1.

9. The seed of claim 8, wherein the QTL is homozygously present.

10. A *Capsicum annuum* progeny of the plant of claim 1, wherein the progeny comprises the QTL as defined in claim 1.

11. The progeny of claim 10, wherein the QTL is present in a homozygous state.

12. The *Capsicum annuum* progeny of a plant grown from a seed of the plant of claim 1, wherein the progeny comprises the QTL as defined in claim 1.

13. The progeny of claim 12, wherein the QTL is present in a homozygous state.

14. The *Capsicum annuum* progeny of a plant grown from a seed capable of growing into the plant of claim 1, wherein the progeny comprises the QTL as defined in claim 1.

15. The progeny of claim 14, wherein the QTL is present in a homozygous state.

16. A *Capsicum annuum* propagation material derived from the plant of claim 1, wherein the propagation material comprises the QTL as defined in claim 1.

17. The propagation material of claim 16, wherein the QTL is present in a homozygous state.

18. A *Capsicum annuum* propagation material derived from a seed of the plant of claim 1, or from a plant grown from said seed, wherein the propagation material comprises the QTL as defined in claim 1.

19. The propagation material of claim 18, wherein the QTL is present in a homozygous state.

20. A *Capsicum annuum* propagation material derived from a seed capable of growing into the plant of claim 1, or from a plant grown from said seed, wherein the propagation material comprises the QTL as defined in claim 1.

21. The propagation material of claim 20, wherein the QTL is present in a homozygous state.

22. A propagation material capable of growing into the plant of claim 1.

23. The propagation material of claim 16, wherein the propagation material comprises a callus, microspore, pollen, ovary, ovule, embryo, embryo sac, egg cell, cutting, root, stem, cell, protoplast, leaf, cotyledon, hypocotyl, meristematic cell, root, root tip, microspore, anther, flower, seed or stem; or a part or tissue culture thereof.

24. The propagation material of claim 18, wherein the propagation material comprises a callus, microspore, pollen, ovary, ovule, embryo, embryo sac, egg cell, cutting, root, stem, cell, protoplast, leaf, cotyledon, hypocotyl, meristematic cell, root, root tip, microspore, anther, flower, seed or stem; or a part or tissue culture thereof.

25. The propagation material of claim 20, wherein the propagation material comprises a callus, microspore, pollen, ovary, ovule, embryo, embryo sac, egg cell, cutting, root, stem, cell, protoplast, leaf, cotyledon, hypocotyl, meristematic cell, root, root tip, microspore, anther, flower, seed or stem; or a part or tissue culture thereof.

26. The propagation material of claim 22, wherein the propagation material comprises a callus, microspore, pollen, ovary, ovule, embryo, embryo sac, egg cell, cutting, root, stem, cell, protoplast, leaf, cotyledon, hypocotyl, meristematic cell, root, root tip, microspore, anther, flower, seed or stem; or a part or tissue culture thereof.

27. A pepper fruit, or a part thereof, from the plant of claim 1, wherein the pepper fruit or part thereof comprises the QTL as defined in claim 1.

28. A pepper fruit, or a part thereof, from a plant grown from a seed of the plant of claim 1, wherein the pepper fruit or part thereof comprises the QTL as defined in claim 1.

29. A pepper fruit, or a part thereof, from a plant grown from a seed capable of growing into the plant of claim 1, wherein the pepper fruit or part thereof comprises the QTL as defined in claim 1.

* * * * *

SEQUENCE LISTING

```
<160> NUMBER OF SEQ ID NOS: 8

<210> SEQ ID NO 1
<211> LENGTH: 113
<212> TYPE: DNA
<213> ORGANISM: Capsicum baccatum
<220> FEATURE:
<221> NAME/KEY: source
<222> LOCATION: 1..113
<223> OTHER INFORMATION: /organism="Capsicum baccatum"
      /mol_type="unassigned DNA"

<400> SEQUENCE: 1
ttaaactatc cttttccaat caccacatgm ccaggcttcg acttgctaaa agctcttttc    60
agcatttgac cctccgcaga gagagcggtt gaaagcttgt aaacatgaac aag          113

<210> SEQ ID NO 2
<211> LENGTH: 113
<212> TYPE: DNA
<213> ORGANISM: Capsicum annuum
<220> FEATURE:
<221> NAME/KEY: source
<222> LOCATION: 1..113
<223> OTHER INFORMATION: /organism="Capsicum annuum"
      /mol_type="unassigned DNA"

<400> SEQUENCE: 2
ttaaactatc cttttccaat caccacatgm acaggcttcg acttgctaaa agctcttttc    60
agcatttgac cctccgcaga gagagcggtt gaaagcttgt aaacatgaac aag          113

<210> SEQ ID NO 3
<211> LENGTH: 100
<212> TYPE: DNA
<213> ORGANISM: Capsicum baccatum
<220> FEATURE:
<221> NAME/KEY: source
<222> LOCATION: 1..100
```

```
<223> OTHER INFORMATION: /organism="Capsicum baccatum"
      /mol_type="unassigned DNA"

<400> SEQUENCE: 3
gacttgtttt gtctgggatt gaatgttttt tattgttgta gtagtagcag aagcaaaaaa    60
tgttgatgta aattatgaaa tattactgct aatatttgtg                         100

<210> SEQ ID NO 4
<211> LENGTH: 100
<212> TYPE: DNA
<213> ORGANISM: Capsicum annuum
<220> FEATURE:
<221> NAME/KEY: source
<222> LOCATION: 1..100
<223> OTHER INFORMATION: /organism="Capsicum annuum"
      /mol_type="unassigned DNA"

<400> SEQUENCE: 4
gacttgtttt gtctgggatt gaatgttttt tattgttgta gtagtagcag aagcgaaaaa    60
tgttgatgta aattatgaaa tattactgct aatatttgtg                         100

<210> SEQ ID NO 5
<211> LENGTH: 157
<212> TYPE: DNA
<213> ORGANISM: Capsicum baccatum
<220> FEATURE:
<221> NAME/KEY: source
<222> LOCATION: 1..157
<223> OTHER INFORMATION: /organism="Capsicum baccatum"
      /mol_type="unassigned DNA"

<400> SEQUENCE: 5
tcagccagta ctagttctgc tctccaaacc tggttaggaa aaaaaacagc tacatgaata    60
gtatataatg cactaaaaam ytcagatagc taaacgagaa cgaacaatag tcactactgg   120
gaywsrsaam mvdtdttwac actaaatgga aaataca                            157

<210> SEQ ID NO 6
<211> LENGTH: 157
<212> TYPE: DNA
<213> ORGANISM: Capsicum annuum
<220> FEATURE:
<221> NAME/KEY: source
<222> LOCATION: 1..157
<223> OTHER INFORMATION: /organism="Capsicum annuum"
      /mol_type="unassigned DNA"

<400> SEQUENCE: 6
tcagccagta ctagttctgc tctccaaacc tggttaggaa aaaaaacagc tacatgaata    60
gtatataatg cactaaaaam ytcagatagc taaatgagaa cgaacaatag tcactactgg   120
gaywsrsaam mvdtdttwac actaaatgga aaataca                            157

<210> SEQ ID NO 7
<211> LENGTH: 111
<212> TYPE: DNA
<213> ORGANISM: Capsicum baccatum
<220> FEATURE:
<221> NAME/KEY: source
<222> LOCATION: 1..111
<223> OTHER INFORMATION: /organism="Capsicum baccatum"
      /mol_type="unassigned DNA"

<400> SEQUENCE: 7
ctgcaccagc tctgcttgca ctaaaacaga aacgactgac gtttacctgg cttgatgggg    60
```

```
aagcacagaa agtgagcacc tctcttcaaa tgtttgcatt cctttggtta a            111
```

<210> SEQ ID NO 8
<211> LENGTH: 111
<212> TYPE: DNA
<213> ORGANISM: Capsicum annuum
<220> FEATURE:
<221> NAME/KEY: source
<222> LOCATION: 1..111
<223> OTHER INFORMATION: /organism="Capsicum annuum"
      /mol_type="unassigned DNA"

<400> SEQUENCE: 8

```
ctgcaccagc tctgcttgca ctaaaacaga aacgactgac gtttacctgg cttgatgggg   60
aagcacagaa agtgagcact tctcttcaaa tgtttgcatt cctttggtta a            111
```